United States Patent [19]

Matsutani et al.

[11] Patent Number: 4,910,377
[45] Date of Patent: Mar. 20, 1990

[54] SYSTEM FOR CREATING HOLES IN SURGICAL NEEDLE MATERIALS

[75] Inventors: Kanji Matsutani; Tadashi Otsuka, both of Shioya, Japan

[73] Assignee: Matsutani Seisakusho Co., Ltd., Tochigi, Japan

[21] Appl. No.: 348,953

[22] Filed: May 8, 1989

[30] Foreign Application Priority Data

Aug. 11, 1988 [JP] Japan ................ 63-198992

[51] Int. Cl.⁴ .............................. B23K 9/00
[52] U.S. Cl. .................. 219/121.19; 219/121.32; 219/121.68; 219/121.82; 219/121.83
[58] Field of Search ............ 219/121.12, 121.35, 219/121.83, 121.85, 121.19, 121.20, 121.31, 121.32, 121.68, 121.69, 121.70, 121.71, 121.78, 121.82, 121.6

[56] References Cited

U.S. PATENT DOCUMENTS

4,700,043 10/1987 Matsutani .................. 219/121.69

FOREIGN PATENT DOCUMENTS

| | | |
|---|---|---|
| 52-111294 | 9/1977 | Japan . |
| 55-43691 | 3/1980 | Japan . |
| 56-37918 | 9/1981 | Japan . |
| 59-110532 | 6/1984 | Japan . |
| 60-170590 | 9/1985 | Japan . |
| 60-184485 | 9/1985 | Japan . |
| 61-30250 | 2/1986 | Japan . |
| 63-140789 | 6/1988 | Japan . |

*Primary Examiner*—C. L. Albritton
*Attorney, Agent, or Firm*—Wegner & Bretschneider

[57] ABSTRACT

There is disclosed a system for creating holes in surgical needle materials, respectively. A large number of needle materials are held by a holder. An image of the proximal end faces of the needle materials is picked up by an image pickup device. A moving mechansim is operated in accordance with this image information so as to move at least one of a beam emitting device and the holder in a direction intersecting the axes of the needle materials and the axis of an energy beam to be emitted from the beam emitting device, so that the energy beam to be emitted can sequentially coincide with the axes of the needle materials. Then, the energy beam is sequentially applied to the proximal end faces of the needle materials to create the respective holes therein. When an electron beam is used as the energy beam, the electron beam is deflected by deflecting coils so that the electron beam can coincide with the axis of a selected one of the needle materials.

11 Claims, 9 Drawing Sheets

3
SYSTEM FOR CREATING HOLES IN SURGICAL NEEDLE MATERIALS

BACKGROUND OF THE INVENTION

Field of the Invention

This invention relates to a system for creating holes in proximal end faces of surgical needle materials, respectively.

A surgical needle of a so-called eyeless type is formed by creating a hole in the proximal end of a straight needle material along the axis thereof and then by bending the needle material into a suitable form. Before or after the above bending operation, a thread or gut for surgical suture is inserted at one end into the hole in the needle material, and the proximal end portion of the needle material is deformed by pressing to thereby fasten the inserted thread to the needle material.

Japanese Utility Model Publication No. 37918/81, Japanese Laid-Open (Kokai) Utility Model Application No. 43691/80, and Japanese Laid-Open (kokai) Patent Application Nos. 111294/77, 110532/84, 170590/85, 184485/85, 30250/86 and 140789/88 discloses apparatus for creating holes in needle materials. In such conventional apparatus, needle materials are moved one by one to a predetermined position where an energy beam such as a laser beam is applied to the center of the proximal end of each needle material to form a thread-insertion hole therein. With this method, however, the needle materials have to be brought into the above predetermined position one by one either manually or mechanically so that each needle material can be aligned with the axis of the energy beam. This has failed to provide a high productivity. Particularly when the needle materials to be processed are thin or when they are not circular in cross-section at the portion thereof extending from a pointed distal end to a point intermediate the opposite ends, the above positioning operation has been rather difficult.

U.S. Pat. No. 4,700,043 which is related to the present invention describes that holes are formed respectively in a plurality of needle materials joined together into a bundle by metal of a low melting point. However, this U.S. Patent does not disclose an image pickup means and a moving mechanism for moving the group of needle materials.

SUMMARY OF THE INVENTION

It is therefore an object of this invention to provide a system by which holes can be created respectively in a plurality of surgical needle materials quite efficiently in a manner suited for mass production of the surgical needles.

According to a first aspect of the invention, there is provided a system for creating holes in surgical needle materials, comprising:

(a) beam emitting means for emitting an energy beam;

(b) holder means for holding a number of the needle materials in such a manner that the needle materials are disposed in parallel relation to the energy beam to be emitted;

(c) image pickup means for picking up an image of proximal end faces of the needle materials to output an image information representative of the image;

(d) moving means for moving at least one of the beam emitting means and the holder means in a direction intersecting the axes of the needle materials and the axis of the energy beam; and (e) control means operable in accordance with the image information so as to control the operation of the moving means to sequentially coincide the axes of the needle materials with the axis of the energy beam to be emitted, the control means being also operable to control the operation of the beam emitting means so as to cause the beam emitting means to apply the energy beam to the proximal end face of each needle material whose axis coincides with the energy beam, thereby creating a hole in the proximal end face.

According to a second aspect of the invention, there is provided a system for creating holes in surgical needle materials, comprising:

(a) holder means for holding a number of the needle materials;

(b) image pickup means for picking up an image of proximal end faces of the needle materials to output an image information representative of the image;

(c) beam emitting means for emitting an electron beam;

(d) coil means for deflecting the electron beam to determine a path of travel of the electron beam; and (e) control means operable in accordance with the image information so as to control the operation of the coil mean to sequentially bring a distal end of the path of travel of the electron beam into registry with the axes of the needle materials, the control means being also operable to control the operation of the beam emitting means so as to cause the beam emittingmmeans to apply the electron beam to the proximal end face of each needle material disposed in registry with the electron beam, thereby creating a hole in the proximal end face.

DESCRIPTION OF THE PREFERRED EMBODIMENTS OF THE INVENTION

The invention will now be described with reference to the drawings.

Figure 1:
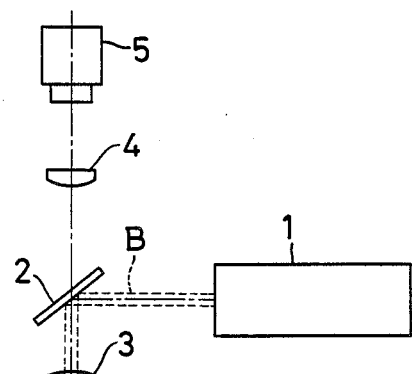
FIG. 1 is a schematic view of a hole-creating system using a laser beam, provided in accordance with the present invention.

FIG. 1 is a schematic view of one preferred embodiment of a hole-creating system of the present invention. The system comprises a beam emitting device 1 which emits a laser beam B as an energy beam in a horizontal direction. A semitransparent mirror 2, which may be a dichroic mirror, is disposed forwardly of the beam emitting device 1, the mirror 2 being arranged at an angle of 45 degrees. A convergent lens 3 is disposed beneath the semi-transparent mirror 2, and a correcting lens 4 and a television camera 5 (image pickup means) are disposed above the semi-transparent mirror 2 in this order from the mirror 2. The television camera 5 has a solid image sensor of CCD or the like serving as a light-receiving surface. The optical axis of the television camera 5 is vertical and coincides with the optical axis of the laser beam B reflected by the semi-transparent mirror 2.

A group A of surgical needle materials N are arranged below the lens 3. The group A of surgical needle materials N are held by a holder 40 (see FIG. 2) in such a manner that the axis of each needle material N is parallel to the axis of the laser beam B. In other words, a large number of needle materials N are disposed vertically. The holder 40 is moved in horizontal and vertical directions by a moving mechanism 20 (see FIG. 2) later described. The laser beam B emitted by the beam emitting device 1 is reflected by the semi-transparent mirror 2, and is converged by the convergent lens 3, and is applied to the needle material N to create a hole therein.

Each needle material N is straight and has a proximal end face disposed perpendicular to the axis of the needle material N. The needle material N is beforehand subjected to a grinding operation so that it has a pointed distal end and has a portion of a circular or a non-circular cross-section extending from its intermediate point to the pointed distal end. The needle material N may not be subjected to a grinding operation beforehand so that it has a circular cross-section throughout its entire length.

A thread for surgical suture is inserted at ne end into the hole formed in the proximal end portion of the needle material N, and then this proximal end portion is deformed by pressing to fasten the thread to the needle material N. The needle material is suitably bent before or after the suture thread is secured thereto, thus providing a surgical needle (finish product).

Figure 2:
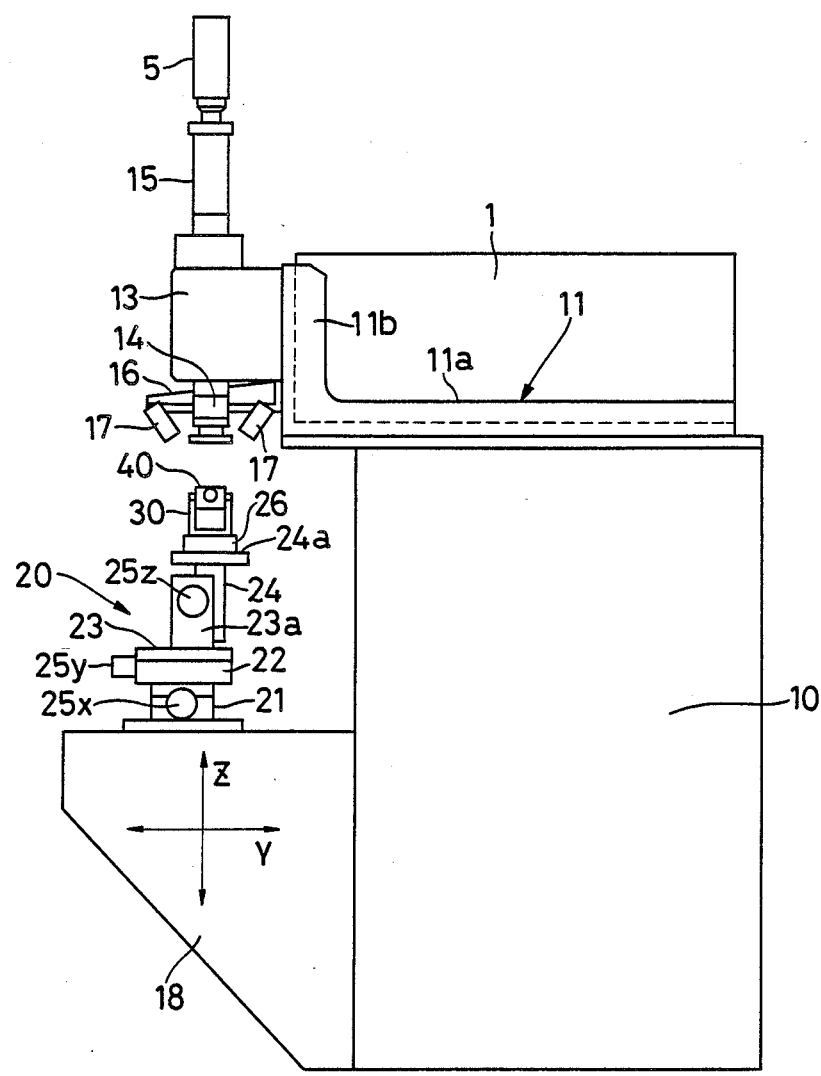
FIG. 2 is a side-elevational view of the system.

FIG. 2 shows the above system of the invention more specifically. A frame 11 of an L-shape is fixedly mounted on a base 10. The beam emitting device 1 is fixedly mounted on a horizontal portion 11a of the frame 11. A case 13 containing the semi-transparent mirror 2 therein is fixedly mounted on a vertical portion 11b of the frame 11. A tube 14 containing the convergent lens 3 is fixedly mounted on the underside of the case 13. A tube 15 containing the correcting lens 4 is fixedly mounted on the top of the case 13, and the television camera 5 is fixedly mounted on the upper end of the tube 15. A pair of flood lamps 17 are fixedly mounted on the vertical portion 11b of the frame 11 through a bracket 16, the flood lamps 17 serving to apply light (visible radiation) onto the large number of needle materials N so that the television camera 5 can pick up a good picture thereof.

An auxiliary base 18 is fixedly mounted on the side of the base 10, and the moving mechanism 20 is mounted on the auxiliary base 18. The holder 40 is supported on the upper end of the moving mechanism 20.

The moving mechanism 20 is well-known and will therefore be described briefly. The moving mechanism 20 comprises a base 21 fixedly secured to the auxiliary base 18. An X-stage 22 is mounted on the base 21 so as to be horizontally movable in an X-axis direction (i.e., in a direction perpendicular to the sheet of FIG. 2). A Y-stage 23 is mounted on the X-stage 2 so as to be horizontally movable in a Y-axis direction. The Y-stage 23 has an upstanding portion 23a on which a Z-stage is mounted so as to be movable in a Z-axis direction, that is, vertically. The positions of the three stages 22, 23 and 24 are controlled by pulse motors 25x, 25y and 25z, respectively, with high precision. These pulse motors may be replaced by servo motors.

Figure 3:
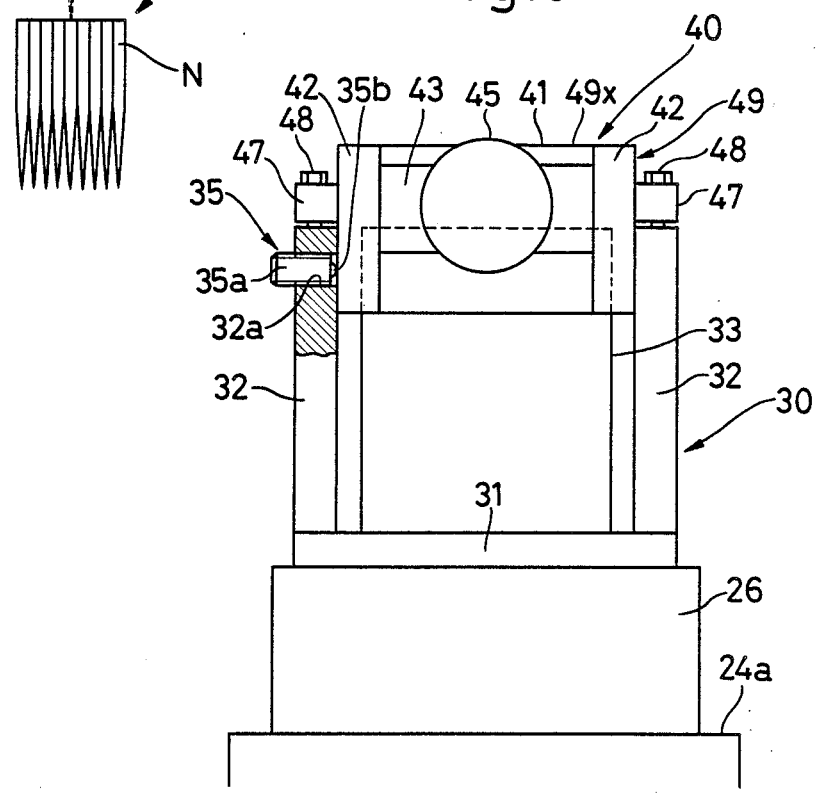
FIG. 3 is an enlarged side-elevational view of a portion of the system, showing a support base and a needle material holder.

The Z-stage 24 has a horizontal portion 24a on which a spacer 26 is fixedly mounted as best shown in FIG. 3. A support base 30 is fixedly mounted on the upper surface of the spacer 26. The support base 30 comprises a bottom plate 31, a pair of opposed side plates 32 and 32 extending upwardly from the bottom plate 31 to the same height or level, and a rear plate 33. A threaded hole 32a is formed through the left-hand side plate 32 (FIG. 3), and an urging means 35 is received in the threaded hole 32a. The urging means 35 comprises an elongated body 35a threaded into the threaded hole 32a, a spring (not shown) received within a ball-receiving hole formed in a right-hand end face of the body 35a (FIG. 3), and a ball 35b received in the ball-receiving hole in a manner to partially extend exteriorly of this hole and is urged by the spring in a right-hand direction.

Figure 4:
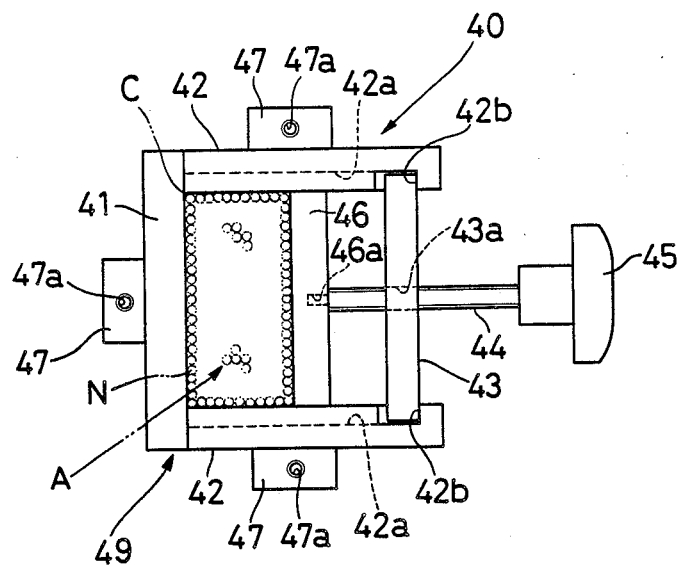
FIG. 4 is a plan view of the holder of FIG. 3.
Figure 5:
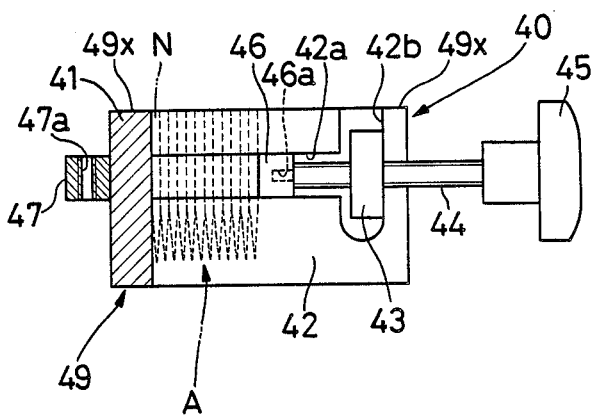
FIG. 5 is a cross-sectional view of the holder.

The holder 40 holding the group A of needle materials N is supported on the support base 30. As shown in FIGS. 3 to 5, the holder 40 comprises a frame 49 which comprises a rear plate 41 and a pair of opposed side plates 42 and 42 fixedly secured respectively to the opposite side portions of the rear plate 41. A pair of guide grooves 42a and 42a are formed respectively in the inner surfaces of the side plates 42 and 42 and extend horizontally. A pair of vertically-extending retainer grooves 42b and 42b are also formed respectively in the inner surfaces of the side plates 42 and 42 adjacent to their one ends remote from the rear plate 41. The pair of guide grooves 22a and 42a are continuous with the pair of retainer grooves 42b and 42b, respectively. Opposite ends of a retainer member 43 are loosely fitted respectively in the retainer grooves 42b and 22b formed respectively in the pair of side plates 42 and 42. A threaded hole 43a is formed through the central portion of the retainer member 43, and a threaded rod 44 is thread through the threaded hole 43a. A thumb piece 45 is fixed secured to one end of the threaded rod 44, and the other end of the threaded rod 44 is rotatably fitted in a hole 46a formed in a holder member 46. The opposite ends of the holder member 46 are slidably received respectively in the pair of guide grooves 42a and 42a so that the holder member 46 can move along these guide grooves. Flanges 47 each having a vertical threaded hole 47a are fixedly secured to the outer surfaces of the rear plate 41 and the two side plates 42 and 42, respectively.

When the group of needle materials N are to e held by the holder 40, the holder 40 is first placed on a horizontal surface in such a manner that the rear plate 41 is disposed below the holder member 46. In this condition, a large number of (for example, several hundreds to several tens of thousands) needle materials N are piled up on the rear plate 41, with their proximal end faces directed toward a surface 49x of the frame 49.

Then, the thumb piece 45 is turned to move the holder member 46 and the retainer member 43 away from each other, so that the holder member 46 is brought into contact with the large number of needle materials N, with the opposite ends of the retainer member 43 held respectively against one side walls of the two retainer grooves 42b and 42b remote from the holder member 46. Thus, the large number of needle materials N are held in the space enclosed by the holder member 46, the rear plate 41 and the pair of side plates 42 and 42 under a relatively weak force applied by the holder member 46.

Then, the surface 49x of the frame 49 is directed downwardly with the proximal end faces of the needle materials N also directed downwardly, and in this condition the holder 40 is placed on a flat horizontal surface of a vibrating device (not shown). Then, the vibrating device is operated to impart high frequency vibration to the needle materials N so that the needle materials N move downwardly due to their own weights until their proximal end faces abut against the flat surface of the vibrating device. Thus, the proximal end faces of all the needle materials N lie flush with the surface 49x of the frame 49.

Then, the thumb piece 45 is further turned to press the holder member 46 against the needle materials N more firmly, so that the needle materials N are formed into the group A in which the needle materials N can not be moved or displaced relative to one another.

The holder 40 thus firmly holding the large number of needle materials N is supported by the support base 30 in such a manner that the lower end portion of the frame 49 received in the support base 30, with the surface 49x of the frame directed upwardly. More specifically, adjusting bolts 48 are beforehand threaded into the threaded holes 47a of the flanges 47 of the holder 40, and the lower ends of these bolts 48 abut against the upper surface of the support base 30 to thereby support the holder 40 on the support base 30. By adjusting the amount of tightening (insertion) of each bolt 48, the surface 49x of the frame 49 of the holder 40 is made horizontal, which means that the proximal end faces of the needle materials N are disposed in a common horizontal plane, with their axes disposed vertically.

In this supported condition of the holder 40, the rear plate 41 of the holder 40 is held in contact with the inner surface of the rear plate 33 of the support base 30. Also, as shown in FIG. 3, the ball 35b of the urging means 35 urges the left-hand side plate 42, so that the other or right-hand side plate 42 is held against the inner surface of the right-hand side plate 32 of the support base 30. Therefore, a reference point C lying on the intersection between the inner surface of the rear plate 41 and the inner surface of the other side plate 42 is disposed at a predetermined position relative to the support base 30. When the moving mechanism 20 is in its initial condition, the reference point C coincides with the optical axis of the laser beam B and the optical axis of the television camera 5.

Figure 6:
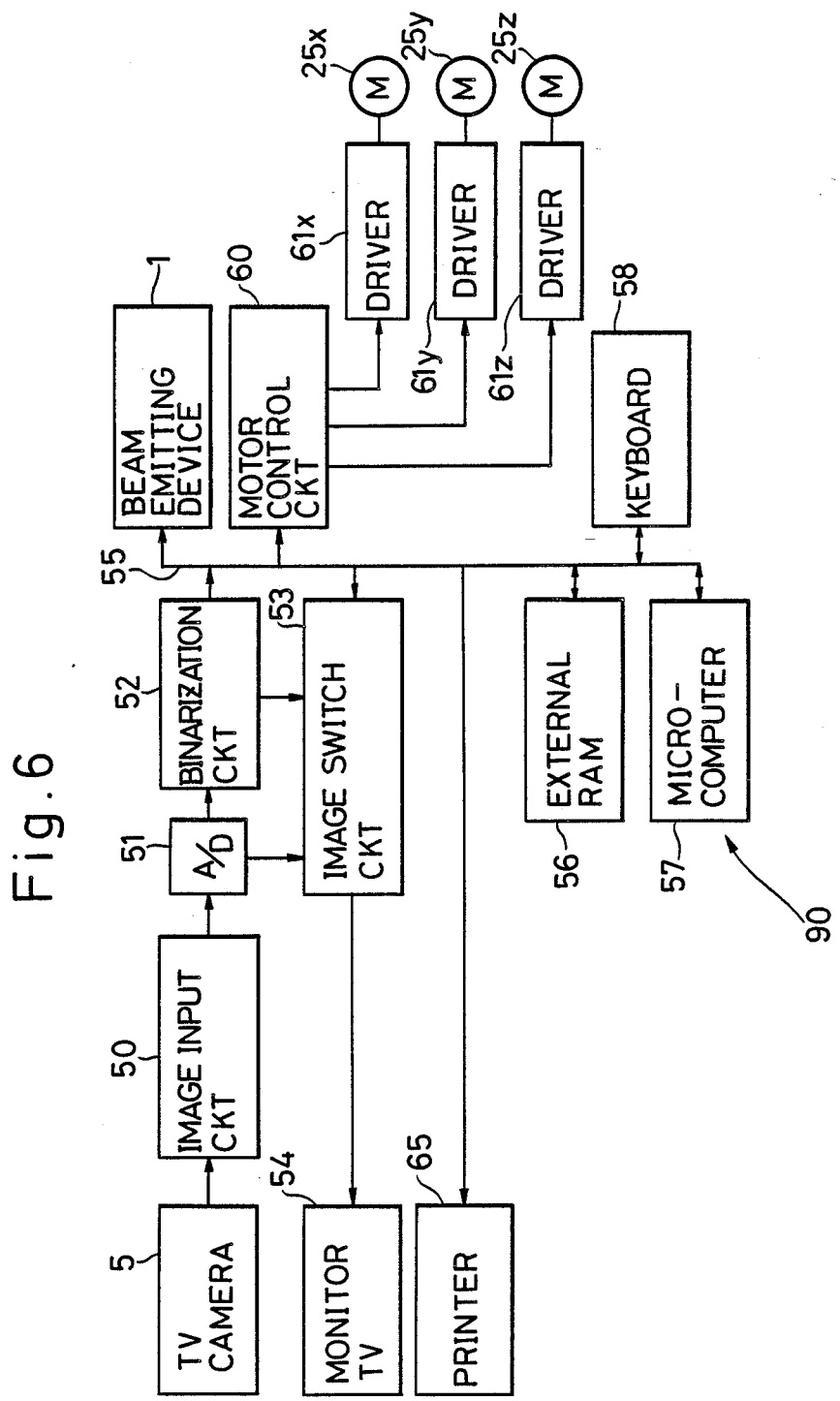
FIG. 6 is a block diagram of the system.

A control circuit 90 for controlling the operations of the moving mechanism 20 and the beam emitting device 1 will now be described with reference to FIG. 6. An image information picked up by the television camera 5 is inputted to an image input circuit 50 and is sent to an analog-to-digital (A/D) converter 51 where the image information is digitized. More specifically, the picture elements of the image picked up by the television camera 5 are represented in terms of 256 luminance (brightness) levels. The image information of the A/D converter 51 is fed to a binarization circuit 5 where this information is binarized. More specifically, in the binarization circuit 52, the luminance level of each picture element is binarized, using a predetermined luminance level (for example, of 150) as a threshold value. In accordance with an instruction signal from a keyboard 58 later described, an image switch circuit 53 selects one of the outputs of the A/D converter 51 and the binarization circuit 52 representing the image information, and sends the selected output to a monitor television 54. The needle materials N are displayed on the monitor television 54 on a magnified scale. Particularly when the binarized image information is fed to the monitor television 54, the image having a clear contrast between the black and the white is displayed on the monitor television 54.

The binarized image information is fed via a data bus 55 to an external RAM (random access memory) and is stored therein. A microcomputer 57, the keyboard 58, the beam emitting device 1 and a motor control circuit 60 are connected to the data bus 55. The microcomputer 57 includes a central processing unit (CPU), a read only memory (ROM) storing programs and information of the needle materials, and a RAM for storing the information of the positions of needle materials N. In accordance with an instruction from the microcomputer 57, the motor control circuit 60 sends pulse signals to drivers 61x, 61y and 61z for driving the pulse motors 25x, 25y and 25z, respectively. Optionally, a printer 65 is connected to the data bus 55.

The hole-creating operation to be carried out by the above system will now be described. As described above, since the proximal end faces of the needle materials N held by the holder 40 are at the same level as the upper surface 49x of the frame 49 of the holder 40, it is usually not necessary to control the pulse motor 25z for moving the holder 40 in the Z-axis direction.

When the moving mechanism 20 is in its initial condition, with the reference point C of the holder 40 coinciding with the optical axis of the television camera 5, the television camera 5 picks up a picture of a limited region (i.e., a limited number of needle materials N) in the vicinity of the reference point C.

Information representative of the diameter and material of the needle material N and the depth of the hole to be formed in each needle material N are beforehand stored in the internal RM of the microcomputer 57 through the keyboard 58.

Figure 7:
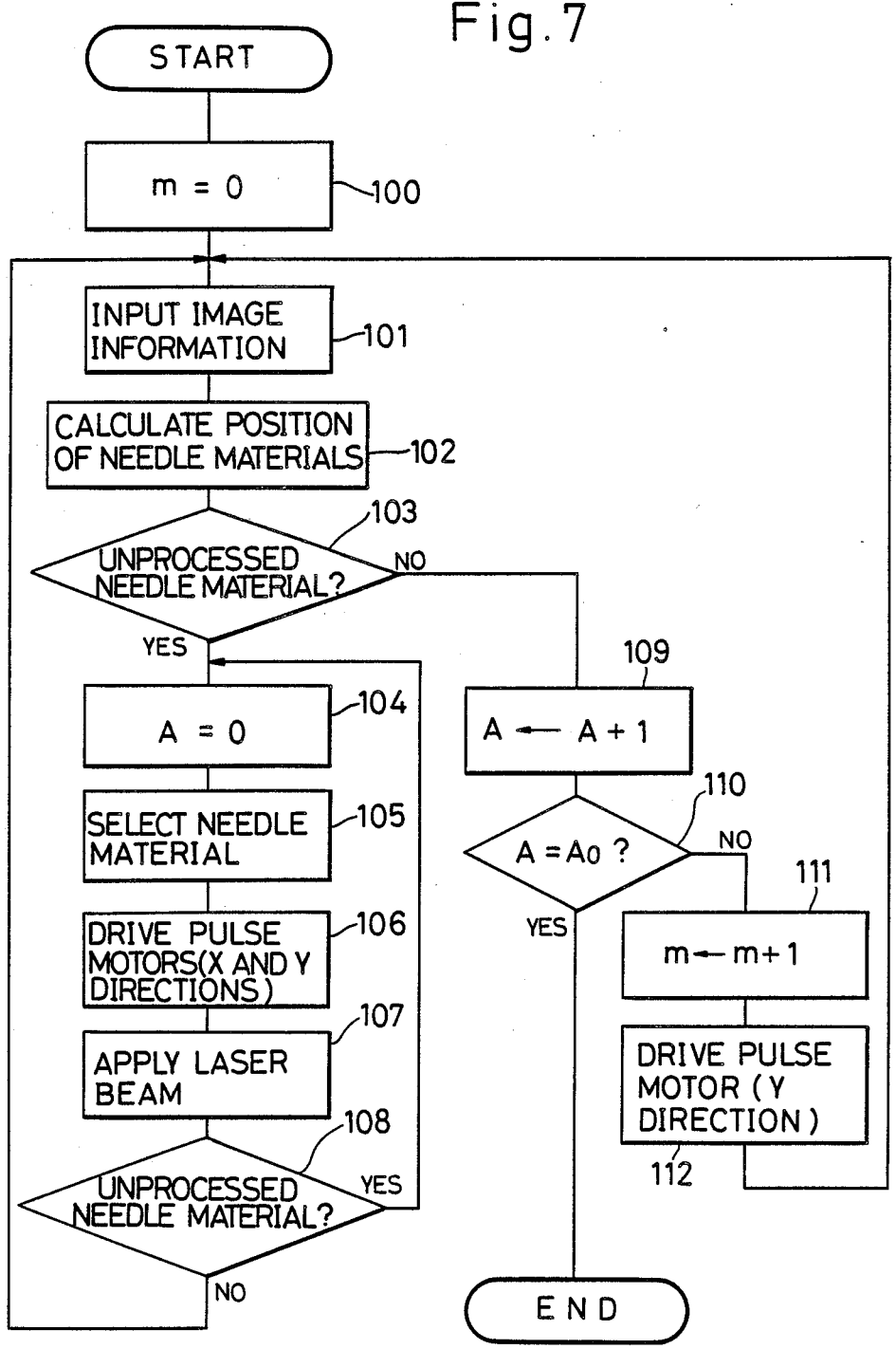
FIG. 7 is a flow chart for a program executed by a microcomputer of FIG. 6.

The program for carrying out the hole creating operation which program is to be executed by the microcomputer 57 will now be described with reference to FIG. 7.

The functions of two registers m' and A' used in this program will first be described. The contents "m" of the register m' represent the Y-coordinate, using the diameters D of the needle materials N as a unit, the Y-coordinate being represented in terms of an integer. The contents A of the register A' substantially represent the number of movement of the holder 40 in the Y-axis direction after there is no unprocessed needle material N.

In accordance with the instruction from the keyboard 58, the microcomputer 57 starts the hole-creating program. First, in Step 100, the register m' is reset. In the next Step 101, the binarized image information stored in the external RAM 56 is inputted to the microcomputer 57. In the next Step 102, in accordance with this image information, a calculation is carried out to determine the positions of the axes of the needle materials N which are picked up by the television camera 5 and disposed in the vicinity of the reference point C. This position information is stored in the internal RAM of the microcomputer 57. The value "zero" of the X-coordinate and the Y-coordinate at this position is represented by the reference point C.

In the next Step 103, it is judged whether or not there is any unprocessed needle material N (in which a hole has not yet been created) among those needle materials N of which positions of the axes are calculated as described above. More specifically, it is judged whether or not there is any unprocessed needle material N whose axes are disposed in the range or area represented by the following formula:

$$mD \leq Y \leq (m+1)D$$

Figure 8:
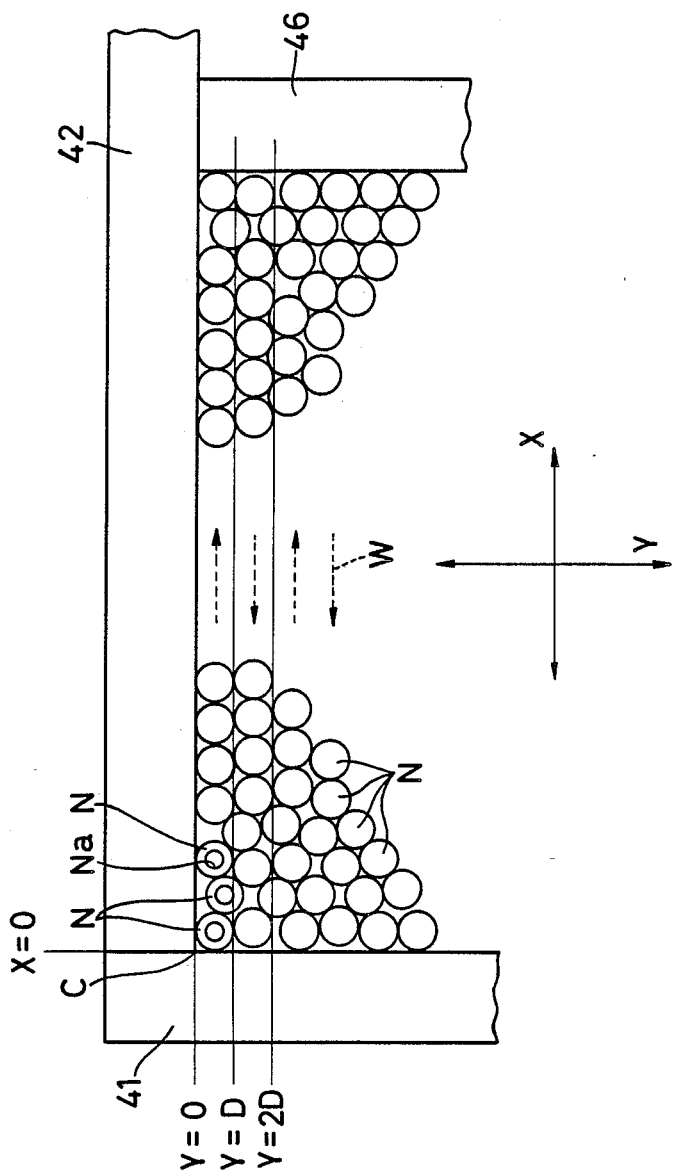
FIG. 8 is an enlarged plan view of a portion of the holder, showing a hole-creating operation.

Immediately after this program is started, the contents "m" of the register m' are zero, and therefore the judgment in Step 103 is carried out with respect to the needle materials N in the range of which outer boundary is spaced a distance of the diameter D from tee inner surface of the side plate 42 of the holder 40 (that is to say, the first row of needle materials N), as shown in FIG. 8.

If the result of the judgment of Step 103 is YES, the program proceeds to the next Step 104 where the register A' is reset. Then, in the next Step 105, the needle material N to be processed is selected. When the contents "m" of the register m' are an even number the unprocessed needle materials N whose axes are disposed in the above range are selected in the order of from the smallest value of the X-coordinate to the largest value. Therefore, in this case, the unprocessed needle material N nearest to the reference point C is first selected.

In the next Step 106, the pulse motors 25x and 25y are driven to move the holder 40 so that the axis of the thus selected needle material N is brought into alignment with the axis of the laser beam B to be emitted. After the positioning of the needle material N is completed, the program proceeds to the next Step 107 where the beam emitting device 1 is operated to apply a laser beam B of a predetermined number of pulses to the central portion of the proximal end face of the needle material N to form a hole Na therein (see FIG. 8). Data of the positions of the axes of the processed needle materials N having respective holes Na are stored in the internal ROM, thereby preventing the processed needle materials N from being subjected to the laser beam B again.

In the next Step 108, it is judged whether or not there is any unprocessed needle material N, as described above for Step 103. If the result is YES, Steps 104 to 107 are repeated. When the hole creating operation is completed with respect to all those needle materials N which are picked up by the television camera 5 and have their axes disposed in the above range, the result of the judgment in Step 108 is NO, and then the program returns to Step 101. As a result, a fresh image information is inputted into the microcomputer 57. This fresh image is picked up by the television camera 5 in such a manner that the optical axis of the television camera 5 is in alignment with the axis of the last processed one of the needle materials N of the preceding image (that is, the one remotest from the reference point C when "m" is an even number). Therefore, the fresh image information includes part of the preceding image information. Then, Steps 102 to 108 are executed with respect to the fresh image information in the manner described above.

In the manner mentioned above, the hole creating operation is completed with respect to all the needle materials N whose axes are disposed in the above range represented by $(mD \leq Y \leq (m+1)D)$. In this case, even when in accordance with the judgment "NO" in Step 108, the program returns to Step 101 to input a fresh information, there is no unprocessed needle material in the above range. As a result, the decision in Step 103 is NO, and therefore the program proceeds to a subroutine beginning from Step 109.

In the above Step 109, the contents "A" of the register A' are incremented by 1. In the next Step 110, it is judged whether or not the contents "A" of the register A' reach a predetermined value Ao. If the result is NO, the program proceeds to Step 111 where the contents "m" of the register m' are incremented by 1. Then, in the next Step 112, the pulse motor 25y is driven to move the needle materials N in the Y-axis direction in an amount corresponding to the diameter D of the needle material N. Then, the program returns to Step 101. Thus, the contents "m" are incremented by 1, for example, to become an odd number (for example, "m" =1). Therefore, in Step 103, it is judged whether there is any unprocessed needle materials N whose axes are disposed in the range of $(D \leq Y \leq 2D)$. In this case, naturally, the result of this judgment is YES, and Steps 104 to 108 are executed as described above. When the contents "m" are an odd number, the unprocessed needle materials N whose axes are disposed in the above range are selected in the order of from the largest value of the X-coordinate to the smallest value. Therefore, in such a case, the unprocessed needle material N remotest from the reference point C is first selected.

Thus, the hole creating operation with respect to the needle materials N are carried out in the order indicated by arrows W in FIG. 8. When all the needle materials N held by the holder 40 are processed to have respective holes, the decision in Step 103 is NO. Thereafter, even when the pulse motor 25y is driven in Step 112, a fresh image picked up by the television camera 5 does not include any unprocessed needle materials N, and therefore a loop from Step 103 to Step 102 through Steps 109, 110, 111, 112 and 101 is repeated. Then, when the contents "A" of the register A' reach the predetermined value Ao, the decision in Step 110 is YES, and the hole creating program is finished.

In the case where the television camera can pick up a very small number of needle materials N (for example, only one needle material), the holder for holding the needle materials N is moved in the X-axis by an amount corresponding to the diameter of the needle material after one needle material is processed to have hole therein. Then, the television camera picks up a fresh image of the next needle material, and in accordance with this fresh image information, the position of the axis of this needle material is detected. Then, the holder is again moved slightly in the X-axis and Y-axis directions to bring the axis of the needle material into alignment with the axis of the laser beam to be emitted. After this positioning operation, the laser beam is applied to form a hole in the needle material.

The focus of the laser beam B may or may not be disposed on the proximal end face of the needle material N. Prior to the hole creating operation, the television camera 5 is set in focus by moving the correcting lens 4 along the axis of the television camera 5.

In the above embodiment, the proximal end faces of all the needle materials N are disposed at the same level or height, and the laser beam B is applied to these proximal end faces in such a manner that its focus is disposed in predetermined positional relation to each of the proximal end face. When the proximal end faces of some of the needle materials N are displaced from the predetermined height beyond an allowable amount, the height of the holder 40 can be adjusted, and thereafter the laser beam is applied. More specifically, the microcomputer 57 detects the image of the diameter of each needle material N in accordance with the binarized image information of the needle materials N. When the diameter of the needle material image differs form the actual diameter, inputted through the keyboard 58, beyond an allowable amount, the position of this needle material is memorized. Then, after the axis of this needle material is caused to coincide with the optical axis of the laser beam B to be emitted, the image information of this needle material which is not binarized is inputted into the microcomputer 57 from the A/D converter 51, and the pulse motor 25z is driven to adjust the height of the holder 40 so that the image of the proximal end face of this needle material N can be represented at a luminance level higher than a relatively high predetermined luminance level. After this adjustment, the laser beam B is applied. Thus, the focus of the laser beam B can be disposed at a predetermined position relative to the proximal end face of the needle material N.

With respect to those needle materials N which have the proximal end faces disposed at heights different from the predetermined height or which can not be recognized with respect to their shape, the positions of such needle materials can be indicated by the printer 65.

The axes of the large number or group of needle material N can be disposed horizontally, in which case the laser beam is applied in a horizontal direction.

In the above embodiment, the holder 40 holding a large number of needle materials N s moved by the moving mechanism 20. However, the holder 40 may be set in a fixed position, in which case the laser beam emitting device, the television camera, etc., are moved by moving mechanisms.

Figure 9:
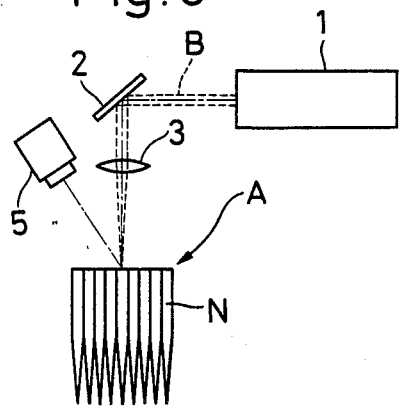
FIG. 9 is a schematic view showing a modified form of the invention.

In the above embodiment, although the optical axis of the laser beam B coincides with the optical axis of the television camera 5, the optical axis of the television camera 5 may be out of alignment with the optical axis of the laser beam B, as shown in FIG. 9. In this case, the television camera 5 is so arranged that its optical axis passes through the axis of the needle material N, aligned with the optical axis of the laser beam B, at the proximal end face thereof. Also, in such a case, the beam emitting device 1 may be so arranged that it emits the laser beam B in a direction parallel to the axis of the needle material N, thereby omitting the semi-transparent mirror 2.

As the energy beam, a electron beam can be used instead of the laser beam. In this case, the beam emitting device emits an electron beam in a direction parallel to the axis of the needle material, and the optical axis of the television camera 5 is out of alignment with the axis of the electron beam. The other parts such as the moving mechanism are the same as in the above embodiment.

Figure 10:
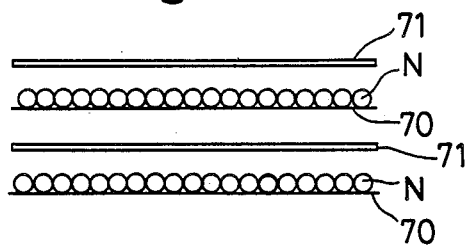
FIG. 10 a plan view of a modified holder.

FIG. 10 shows parts which can be used in combination with the holder 40. More specifically, a row of needle materials N are adhesively held by an adhesive tape 70 in parallel contiguous relation to one another. A plurality of rows of needle materials N carried by the respective adhesive tapes 70 are stacked one upon another, with a sheet or strip 71 of stainless steel or the like interposed between each two adjacent rows. The needle materials N thus stacked can be held by the holder 40 shown in FIGS. 3 to 5. In this case, the sheets 71 are disposed in parallel relation to the rear plate 41 of the holder 40.

Figure 11:
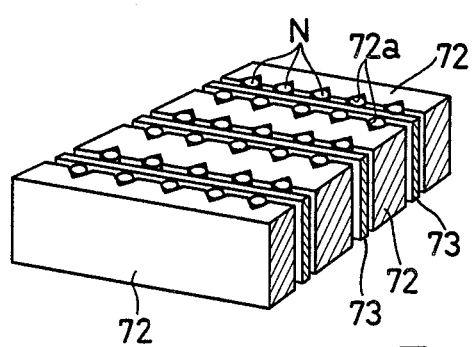
FIGS. 11 and 12 are perspective views of other modified needle material holders, respectively.

FIG. 11 shows a modified holder for holding the needle materials N. This holder comprises a plurality of elongated support plates 72 and a plurality of elongated holder plates 73 connected to the support plates 72 to form a holder assembly, the support plates 72 and the holder plates 73 being arranged alternately. The two support plates 72 disposed respectively at the opposite ends of the holder assembly each has a plurality of V-shaped grooves 72a formed in its inner surface and extending in the direction of its width in parallel relation to one another, the grooves 72a being spaced from one another at an equal interval. Similarly, each of the other support plates 72 has a plurality of V-shaped grooves 72a in each of the opposite surfaces thereof. The needle materials N are received in the V-shaped grooves 72a and held by the holder plates 73 against movement. The support plates 72 and the holder plates 73 are connected together by bolts (not shown) passing through the opposite ends of these plates 72 and 73 and nuts (not shown) threaded on distal ends of the bolts. This holder assembly is set in position in the moving mechanism.

Figure 12:
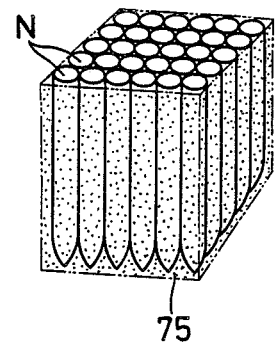

FIG. 12 shows another modified holder for holding the needle materials N. This holder comprises a block of a wax 75 in which a number of needle materials N are arranged in parallel relation and are held against movement relative to one another. For providing this wax holder, the needle materials N are tied together by tee wax 75, with their distal ends held against a flat surface. Then, the needle materials N are cut together with the wax 75 along a plane suitably spaced from their distal ends in perpendicular relation to the axes of the needle materials N. The thus cut ends of the needle materials serve as the proximal end faces which are disposed in a common plane.

Figure 13:
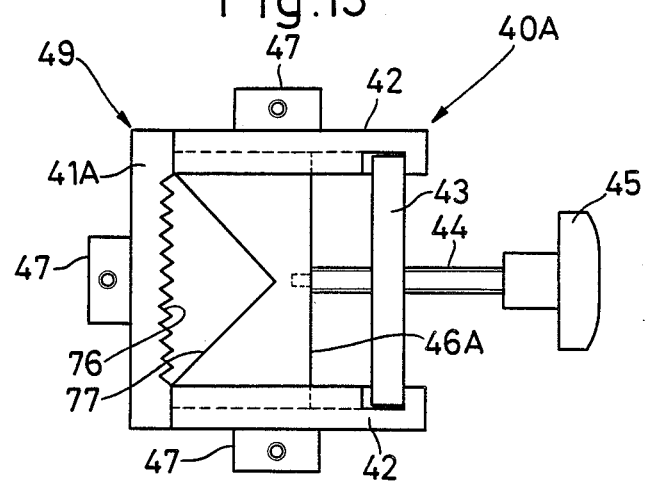
FIG. 13 is a plan view of a further modified needle material holder.

FIG. 13 shows a further modified holder 40A which differs from the holder 40 of FIGS. 4 and 5 only in that a plurality of V-shaped grooves 76 are formed in the inner surface of a rear plate 41A so as to hold the needle materials N in a more stable manner and in that a holder member 46A has a greater dimension in the direction of movement thereof and has a V-shaped notch 77 formed in its surface facing the rear plate 41A.

Further, the holder may comprises a band or a flexible strip for connecting the needle materials N together to form a bundle of needle materials N.

Figure 14:
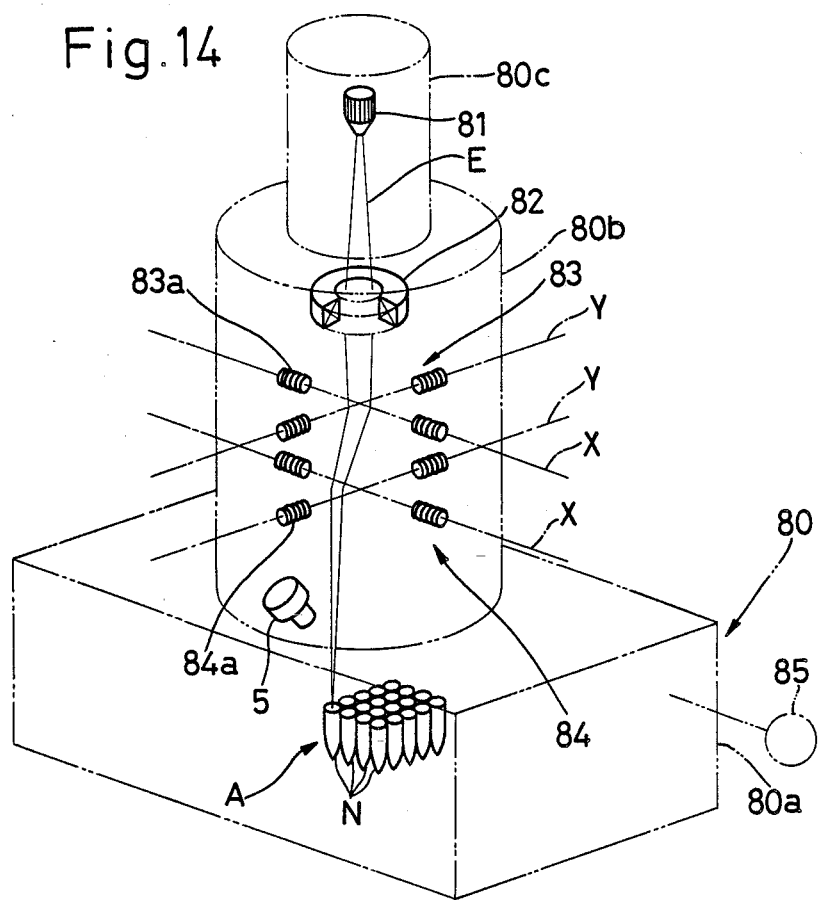
FIG. 14 is a schematic perspective view of modified system, using an electron beam.

FIG. 14 shows a modified system for creating holes in the needle materials in which the hole is created in each needle material by an electron beam without moving the needle materials. More specifically, this system comprises a container 80 which includes a hollow base portion 80a of a rectangular parallelepiped, a tubular portion 80b extending upwardly from an upper surface of the base portion 80a, and a smaller tubular portion 80c extending upwardly from the upper end of the tubular portion 80b.

A group A of vertically-disposed needle materials N are accommodated within the base portion 80a of the container 80. The needle material group A can be placed at a predetermined position, using the support base 30 and the holder 40 shown in FIGS. 3 to 5. The support base 30 is not supported on the moving mechanism 20 (FIG. 2) but is fixedly secured, for example, to the bottom plate of the base portion 80a.

A vacuum pump 85 is connected to the container 80, and after the needle materials N are set in position within the container 80, the vacuum pump 85 is operated to evacuate the interior of the container 80.

A beam emitting device 81 is mounted within the smaller tubular portion 80c. The beam emitting device 81 emits an electron beam E vertically downwardly. A converging coil 82 is mounted within the tubular portion 80b at an upper portion thereof and is disposed beneath the beam emitting device 81. The axis of the converging coil 82 is in alignment with the the axis of the electron beam E. The length of the electron beam E extending between the coil 82 and the converging point of the electron beam E varies in accordance with an electric current flowing through the coil 82.

Two groups of deflecting coils 83 and 84 are mounted within the tubular portion 80b and are disposed below the converging coil 82. The upper group 83 consists of four coils 83a. The axes of these coils 83a perpendicularly intersect the axis of the electron beam E. Two of the four coils 83a are disposed on an X-axis perpendicularly intersecting the axis of the electron beam E while the other two are disposed on a Y-axis perpendicularly intersecting the axis of the electron beam E and the X axis. The four coils 83a are spaced equidistantly from he intersection between the X-axis and the Y-axis. The lower group 84 consists of four coils 84a which are disposed in vertical registry with the coils 83a, respectively.

Figure 15:
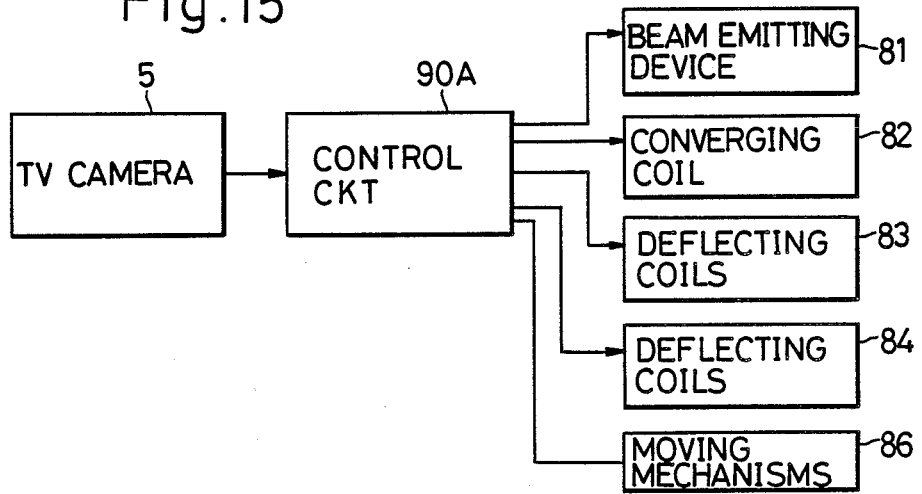
FIG. 15 is a block diagram of the system of FIG. 14.

A television camera 5 is mounted within the vacuum container 80, and this television camera 5 is moved in a horizontal plane by a moving mechanism 86 (shown only in FIG. 15).

Prior to emitting the electron beam E, a control circuit 90A shown in FIG. 15 controls the moving mechanism 86 to move the television camera 5 in a horizontal plane to obtain image information of all the needle materials N. This image information is binarized and stored. In accordance with the binarized image information, the positions of all the needle materials are calculated. Then, in accordance with this position information, the needle materials N to be processed are sequentially selected one after another. In accordance of the position of the selected needle material N, the electric currents flowing through the coil 82, the group 83 of coils 83a and the group 84 of coils 84a are suitably controlled, and the beam emitting device 81 is operated to apply an electron beam E of a predetermined number of pulses to the proximal end face of the selected needle material.

The upper group 83 of deflecting coils vary the angle of deflection of the electron beam E in accordance with the position of the needle material to be processed. The lower group 84 of deflecting coils bring the electron beam E into the vertical direction. As a result, the electron beam E coincides with the axis of the selected needle material N and is applied to the proximal end face thereof to form a hole therein.

By controlling the converging coil 82, the length of the electron beam E extending between the coil 82 and the converging point can be varied in accordance with the position of each needle material N. Therefore, a predetermined positional relation between the converging point of the electron beam E and the proximal end face of the needle material is established. Thus, the holes can be formed in all the needle materials N under the same conditions.

Figure 16:
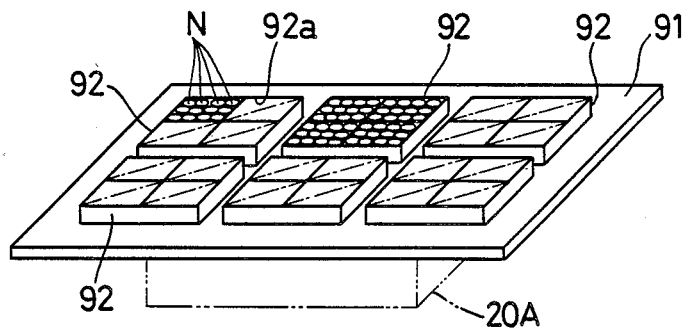
FIG. 16 is a perspective view of a needle material holder applicable to the system of FIG. 14.

In the embodiment of FIG. 14, there may be provided a moving mechanism 20A (FIG. 16) for moving the needle materials N in a horizontal direction. A support base 91 is placed on the moving mechanism 20A, and a plurality of containers (holders) 92 are placed on the support base 91, each container 92 having four compartments 92a. A number of needle materials N are contained in each of the compartments 92a of the container 92. In this embodiment, one of the containers 92 is first set in a operative position where the electron beam E can be applied to the needle materials N contained in the one container 92. After the hole creating operation is completed with respect to all the needle materials N contained in the one container 92, the moving mechanism 20 is driven to bring another container 92, disposed adjacent to the one container 92, to the operative position. With this method, a larger number of needle materials N can be processed to have respective holes.

Figure 17:
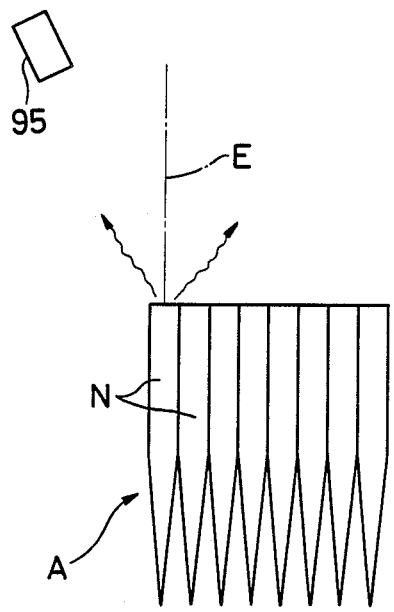
FIG. 17 is another modified system, using an X-ray detecting device.
Figure 18:
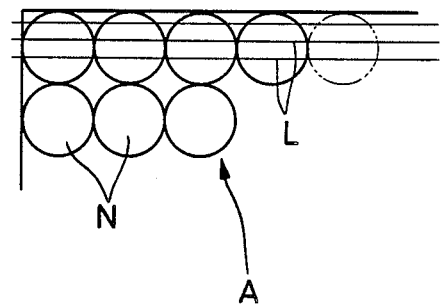
FIG. 18 is a plan view of a portion of a holder of the system of FIG. 17, showing the scanning by the electron beam.

In the case where the hole creating operation is carried out using the electron beam E, the television camera can be replaced by an X-ray detecting device 95 shown in FIG. 17. In this case, prior to creating holes in the needle materials N, the electron beam scans the group A of needle materials N along parallel scanning lines at a lower radiation intensity or level than it is later applied to the needle materials N to form the holes therein. The proximal end faces of the needle materials N to which the electron beam E is applied generate X-rays as indicated by corrugated arrows in FIG. 17. It is necessary that the distance or interval between the scanning lines should be sufficiently smaller than the diameter of the needle material N. An image information of the needle materials N can be obtained from the information of the position of radiation of the electron beam and the information of the amount of the detected X-ray.

What is claimed is:

1. A system for creating holes in surgical needle materials, comprising:
   (a) beam emitting mean for emitting an energy beam;
   (b) holder means for holding a number of the needle materials in such a manner that the needle materials are disposed in parallel relation to he energy beam to be emitted;
   (c) image pickup means for picking up an image of proximal end faces of the needle materials to output an image information representative of said image;
   (d) moving means for moving at least one of said beam emitting means and said holder means in a direction intersecting the axes of the needle materials and the axis of the energy beam; and
   (e) control means operable in accordance with said image information so as to control the operation of said moving means to sequentially coincide the axes of the needle materials with the axis of the energy beam to be emitted, said control means being also operable to control the operation of said beam emitting means so as to cause said beam emitting means to apply the energy beam to the proximal end face of each needle material whose axis coincides with the energy beam, thereby creating a hole in the proximal end face.

2. A system according to claim 1, in which said control means comprises position detecting means operable in accordance with said image information so as to detect the position of the axis of each needle material to produce a position information representative of the position of the axis of the needle material, said control means also comprising selection means responsive to said position information so as to sequentially select the needle materials to be subjected to the hole creating operation, in a predetermined order.

3. A system according to claim 2, in which said selection means sequentially selects those of the needle materials whose axes are disposed at an area extending along an axis perpendicular to the axes of the needle materials, said area having a width substantially equal to the diameter of the needle material.

4. A system according to claim 2, in which said image pickup means comprises a television camera for producing said image information in the analog form, said control means comprising an analog-to-digital converter for converting said analog image information into a digital image information representing said image in various shades, and binarization means for binarizing said digital image information, said position detecting means detecting the positions of the axes of the needle materials in accordance with said binarized image information.

5. A system according to claim 1, in which said moving means comprises a support base for supporting said holder means at a predetermined position, and a first moving mechanism for moving said support base along a first axis perpendicularly intersecting the axis of the energy beam, and a second moving mechanism for moving said support base along a second axis perpendicularly intersecting the axis of the energy beam and said first axis.

6. A system according to claim 5, in which said moving means further comprises a third moving mechanism for moving said support base along the axes of the needle materials, said control means being responsive to said image information so as to control the operation of said third moving mechanism to establish a predetermined positional relation between the focus of the energy beam and the proximal end face of each needle material, so that said beam emitting means can apply the energy beam to the needle materials under substantially the same radiation conditions.

7. A system according to claim 1, in which said holder means comprises a frame for holding a number of the needle materials therein, and a holder member movably mounted on said frame so as to hold the needle materials against movement.

8. A system for creating holes in surgical needle materials, comprising:
(a) holder means for holding a number of the needle materials;
(b) image pickup means for picking up an image of proximal end faces of the needle materials to output an image information representative of said image;
(c) beam emitting means for emitting an electron beam;
(d) coil means for deflecting the electron beam to determine a path of travel of the electron beam; and
(e) control means operable in accordance with said image information so as to control the operation of said coil means to sequentially bring a distal end of said path of travel of the electron beam into registry with the axes of the needle materials, said control means being also operable to control the operation of said beam emitting means so as to cause said beam emitting means to apply the electron beam to the proximal end face of each needle material disposed in registry with the electron beam, thereby creating a hole in the proximal end face.

9. A system according to claim 8, in which said beam emitting means emits the electron beam in a direction parallel to the axes of the needle materials, said coil means comprising a first group of coils and a second group of coils, said first group of coils deflecting the electron beam, emitted from said beam emitting means, in a direction intersecting the axis of the needle material to be subjected to the hole creating operation, and said second group of coils deflecting the electron beam, deflected by said first group of coils, in a direction coinciding with the axis of the needle material to be subjected to the hole creating operation.

10. A system according to claim 9, in which second coil means for converging the electron beam is provided between said beam emitting means and said first group of coils, said control means controlling the operation of said second coil means so as to adjust the length of the electron beam extending between said second coil means and a converging point of the electron beam in accordance with the position of each needle material so that said converging point i disposed at a predetermined position relative to the proximal end face of the needle material to be subjected to the hole creating operation.

11. A system according to claim 8, in which said image pickup means comprises an X-ray detecting device, said control means controlling the operations of said coil means and said beam emitting means prior to creating holes in the needle materials in such a manner that the electron beam scans the proximal end faces of the needle materials along parallel scanning lines at a lower radiation intensity than it is later applied to the needle materials to form the holes therein, the distance between the scanning lines being smaller than he diameter of the needle material, said X-ray detecting device detecting X-rays generated from the proximal ends of the needle materials when the electron beam is applied thereto during the scanning operation, thereby producing a detection signal serving as said image information, said detection signal being sent to said control means.

* * * * *

UNITED STATES PATENT AND TRADEMARK OFFICE
CERTIFICATE OF CORRECTION

PATENT NO. : 4,910,377
DATED : March 20, 1990
INVENTOR(S) : Kanji MATSUTANI et al.

It is certified that error appears in the above-identified patent and that said Letters Patent is hereby corrected as shown below:

In column 12, line 51, change "he" to --the--.

In column 14, line 40, change "i" to --is--.

Signed and Sealed this

Second Day of July, 1991

*Attest:*

HARRY F. MANBECK, JR.

*Attesting Officer*    Commissioner of Patents and Trademarks